United States Patent
Mizuguchi et al.

(10) Patent No.: US 12,296,311 B2
(45) Date of Patent: May 13, 2025

(54) CARBON COMPOUND MANUFACTURING SYSTEM AND METHOD OF CONTROLLING CARBON COMPOUND MANUFACTURING SYSTEM

(71) Applicants: KABUSHIKI KAISHA TOSHIBA, Tokyo (JP); TOSHIBA ENERGY SYSTEMS & SOLUTIONS CORPORATION, Kawasaki (JP)

(72) Inventors: Koji Mizuguchi, Kawasaki (JP); Satoshi Mikoshiba, Yamato (JP); Ryota Kitagawa, Setagaya (JP); Takehiko Muramatsu, Yokohama (JP)

(73) Assignees: KABUSHIKI KAISHA TOSHIBA, Tokyo (JP); TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 54 days.

(21) Appl. No.: 18/323,829

(22) Filed: May 25, 2023

(65) Prior Publication Data
US 2023/0356172 A1    Nov. 9, 2023

Related U.S. Application Data

(62) Division of application No. 17/446,502, filed on Aug. 31, 2021, now Pat. No. 11,701,631.

(30) Foreign Application Priority Data

Mar. 18, 2021    (JP) .................................. 2021-044803

(51) Int. Cl.
B01J 19/00    (2006.01)
B01J 8/08    (2006.01)
(Continued)

(52) U.S. Cl.
CPC .......... B01J 19/0033 (2013.01); B01J 8/082 (2013.01); C07C 1/12 (2013.01); C25B 1/23 (2021.01);
(Continued)

(58) Field of Classification Search
CPC .... B01J 2219/00164; B01J 2219/00182; B01J 8/082; C07C 1/12; C25B 1/23;
(Continued)

(56) References Cited

U.S. PATENT DOCUMENTS

2013/0137783 A1    5/2013    Kumar et al.
2014/0272734 A1    9/2014    Braun
(Continued)

FOREIGN PATENT DOCUMENTS

CA    3 089 119 A1    7/2019
CN    109642332 A    4/2019
(Continued)

OTHER PUBLICATIONS

Japanese Office Action issued Jun. 25, 2024 in Japanese Application 2021-044803, (with unedited computer-generated English translation), 5 pages.
(Continued)

Primary Examiner — Lessanework Seifu
(74) Attorney, Agent, or Firm — Oblon, McClelland, Maier & Neustadt, L.L.P.

(57) ABSTRACT

A carbon compound manufacturing system includes: a recovery unit; a conversion unit; a synthesis unit; a first flow path to supply the supply gas to the recovery unit; a second flow path connecting the recovery and the conversion units; a third flow path connecting the conversion and the synthesis units; at least one of first to third detectors to respectively measure a flow rate of the supply gas flowing through the first flow path to generate a first data signal, a flow rate of
(Continued)

the carbon dioxide flowing through the second flow path to generate a second data signal, and a value of voltage or current to the conversion unit to generate a third data signal; and an integration controller to collate at least one data of the first to third data signals with a corresponding plan data to generate at least one of first to third control signals.

8 Claims, 3 Drawing Sheets

(51) Int. Cl.
  *C07C 1/12* (2006.01)
  *C25B 1/23* (2021.01)
  *C25B 15/023* (2021.01)
  *C25B 15/08* (2006.01)
  *B01D 53/02* (2006.01)
  *B01D 53/14* (2006.01)

(52) U.S. Cl.
  CPC .......... *C25B 15/023* (2021.01); *C25B 15/081* (2021.01); *B01D 53/02* (2013.01); *B01D 53/14* (2013.01); *B01D 2256/22* (2013.01); *B01J 2219/00164* (2013.01); *B01J 2219/00182* (2013.01)

(58) Field of Classification Search
  CPC ... C25B 15/023; C25B 15/081; C25B 15/087; B01D 53/02; B01D 53/14; B01D 2256/22; Y02E 60/36; Y02P 20/133; Y02P 20/15; C10G 2/30; C01B 32/50
  See application file for complete search history.

(56) References Cited

U.S. PATENT DOCUMENTS

| | | |
|---|---|---|
| 2017/0218404 A1 | 8/2017 | Simpson et al. |
| 2019/0226103 A1 | 7/2019 | Kuhl |
| 2020/0002823 A1 | 1/2020 | Ono et al. |
| 2021/0079542 A1 | 3/2021 | Kitagawa et al. |
| 2024/0158321 A1* | 5/2024 | Shimura ............... C25B 15/023 |

FOREIGN PATENT DOCUMENTS

| | | |
|---|---|---|
| DE | 10 2013 102 969 A1 | 8/2014 |
| EP | 4 306 503 A1 | 1/2024 |
| JP | 2018-184655 A | 11/2018 |
| JP | 2019-506165 A | 3/2019 |
| JP | 2019-163530 A | 9/2019 |
| JP | 2020-500258 A | 1/2020 |
| JP | 2021-046574 A | 3/2021 |
| JP | 2022-137754 A | 9/2022 |
| KR | 2017-0026967 A | 3/2017 |
| WO | WO 2018/044720 A1 | 3/2018 |

OTHER PUBLICATIONS

Vincent Dieterich, et al., "Power-to-Liquid via Synthesis of Methanol, DME or Fischer-Tropsch-Fuels: a Review" Energy & Environmental Science, vol. 13, No. 10, Oct. 14, 2020, pp. 3207-3252.

* cited by examiner

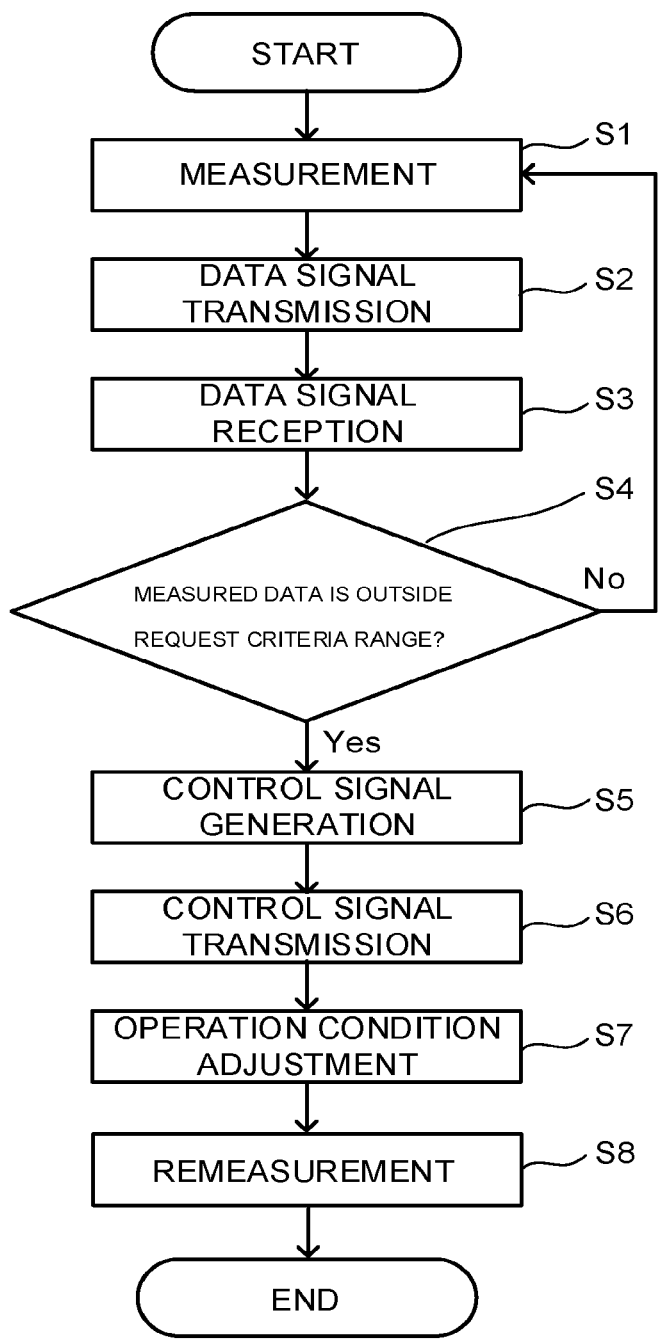

CARBON COMPOUND MANUFACTURING SYSTEM AND METHOD OF CONTROLLING CARBON COMPOUND MANUFACTURING SYSTEM

CROSS-REFERENCE TO RELATED APPLICATION

This application is a divisional of and claims benefit under 35 U.S.C. § 120 to U.S. application Ser. No. 17/446,502, filed Aug. 31, 2021, which is based upon and claims the benefit of priority under 35 U.S.C. § 119 to Japanese Patent Application No. 2021-044803, filed Mar. 18, 2021, the entire contents of each of which are incorporated herein by reference.

FIELD

Embodiments disclosed herein relate to a carbon compound manufacturing system.

BACKGROUND

In recent years, an artificial photosynthesis technology has developed from the viewpoint of energy problems and environmental problems. The technology includes electrochemically reducing carbon dioxide using renewable energy such as sunlight in artificial imitation of photosynthesis to generate a stockable chemical energy resource. A carbon compound manufacturing system realizing the artificial photosynthesis technology includes an electrochemical reaction device having an anode that oxidizes water ($H_2O$) to produce oxygen ($O_2$) and a cathode that reduces carbon dioxide ($CO_2$) to produce a carbon compound. The anode and the cathode of the electrochemical reaction device are connected to a power supply derived from renewable energy such as solar power generation, hydroelectric power generation, wind power generation, or geothermal power generation.

The anode has a structure in which an oxidation catalyst to oxidize water is provided, for example, on the surface of a metal substrate. The cathode has a structure in which a reduction catalyst reducing carbon dioxide reaction is provided, for example, on the surface of a carbon substrate. The cathode obtains reduction potential for carbon dioxide from the power supply derived from renewable energy and thereby reduces carbon dioxide to produce carbon compounds such as carbon monoxide (CO), formic acid (HCOOH), methanol ($CH_3OH$), methane ($CH_4$), ethanol ($C_2H_5OH$), ethane ($C_2H_6$), and ethylene glycol ($C_2H_6O_2$).

BRIEF DESCRIPTION OF THE DRAWINGS

FIG. 3 is a flowchart for explaining an example of a method of controlling the system.

DETAILED DESCRIPTION

A carbon compound manufacturing system of embodiment includes: a recovery unit configured to separate carbon dioxide from a supply gas containing the carbon dioxide; a conversion unit configured to convert the carbon dioxide supplied from the recovery unit into an intermediate compound; a synthesis unit configured to synthesize a carbon compound using the intermediate compound supplied from the conversion unit; a first flow path configured to supply the supply gas to the recovery unit; a second flow path connecting the recovery unit and the conversion unit; a third flow path connecting the conversion unit and the synthesis unit; at least one detector selected from the group consisting of a first detector, a second detector, and a third detector, the first detector being configured to measure a flow rate of the supply gas flowing through the first flow path to generate a first data signal, the second detector being configured to measure a flow rate of the carbon dioxide flowing through the second flow path to generate a second data signal, and the third detector being configured to measure a value of voltage or current supplied to the conversion unit to generate a third data signal; and an integration controller configured to collate measured data in at least one data signal selected from the group consisting of the first to third data signals with a plan data corresponding to the measured data, and generate, according to a collation result, at least one control signal selected from the group consisting of a first control signal for adjusting an operation condition of the recovery unit, a second control signal for adjusting an operation condition of the conversion unit, and a third control signal for adjusting an operation condition of the synthesis unit.

Embodiments will be hereinafter explained with reference to the drawings. Substantially the same components are denoted by the same reference signs and an explanation thereof may be partly omitted in each embodiment explained below. The drawings are schematic and a relation between the thickness and planar dimension, a thickness ratio among the components, and so on may be different from actual ones.

In this description, "connection" includes not only direct connection but also indirect connection unless otherwise designated.

Figure 1:
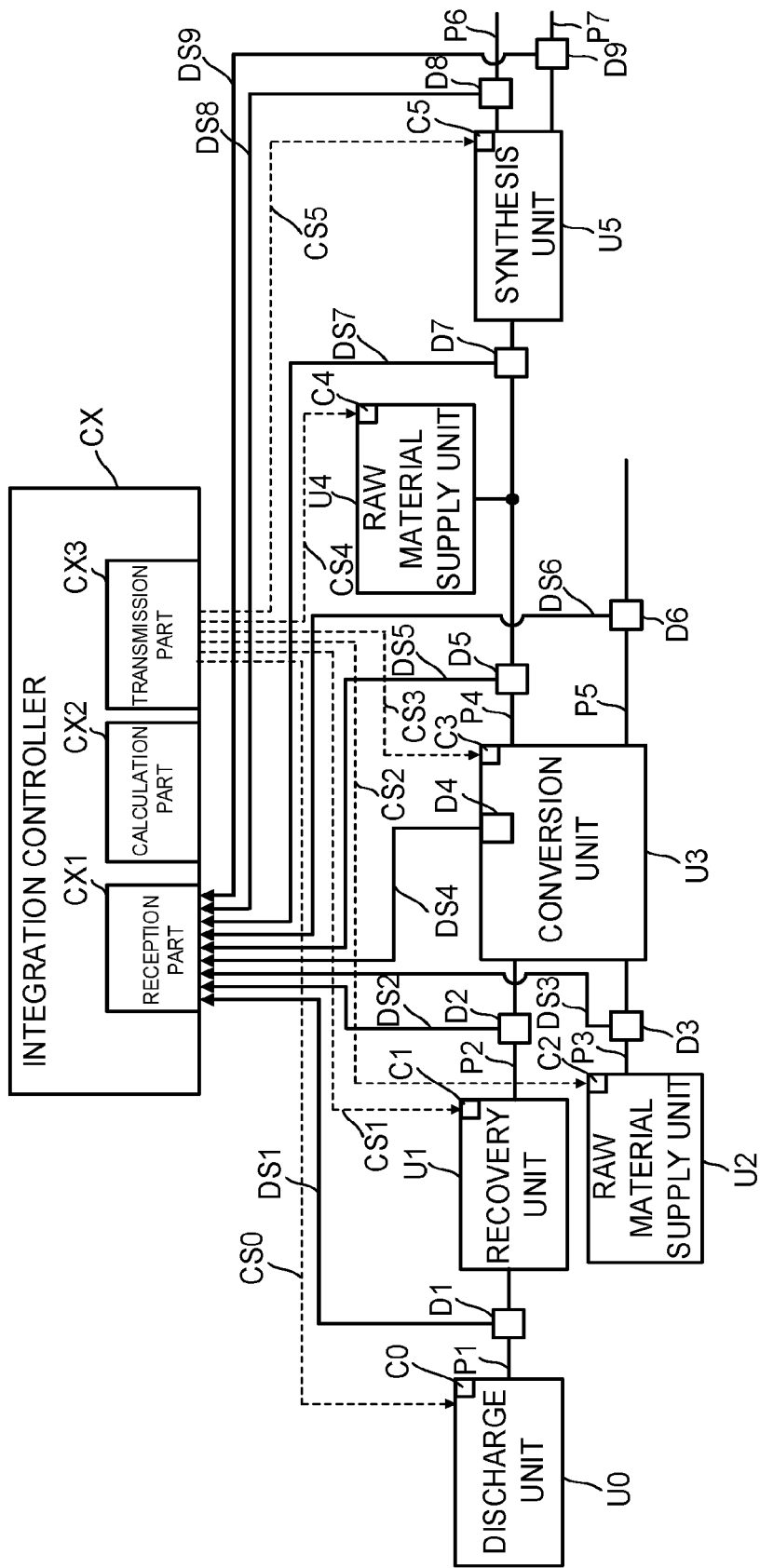
FIG. 1 is a schematic diagram illustrating a configuration example of a carbon compound manufacturing system.

FIG. 1 is a schematic diagram illustrating a configuration example of a carbon compound manufacturing system being one of chemical reaction systems. The system illustrated in FIG. 1 includes an emission unit U0, a recovery unit U1, a raw material supply unit U2, a conversion unit U3, a raw material supply unit U4, a synthesis unit U5, and an integration controller CX. The emission unit U0 may be provided outside the system.

The units U0, U1, U2, U3, U4, U5 illustrated in FIG. 1 have controllers C0, C1, C2, C3, C4, C5, respectively. The number of controllers is not limited to the number illustrated in FIG. 1 and at least one of the above units U0, U1, U2, U3, U4, U5 only has to include the controller.

The system illustrated in FIG. 1 includes flow paths P1, P2, P3, P4, P5 P6, P7 each connected to any of the plurality of units. The flow path P1 connects the emission unit U0 and the recovery unit U1. The flow path P2 connects the recovery unit U1 and the conversion unit U3. The flow path P3 connects the raw material supply unit U2 and the conversion unit U3. The flow path P4 connects the conversion unit U3 and the synthesis unit U5. The flow path P5 is connected to the conversion unit U3. The flow path P6 is connected to the synthesis unit U5. The flow path P7 is connected to the synthesis unit U5. Each flow path is, for example, pipe. The number of flow paths is not limited to the number of the flow paths illustrated in FIG. 1.

The system illustrated in FIG. 1 includes detectors D1, D2, D3, D4, D5, D6, D7, D8. The detector D1 is provided to the flow path P1. The detector D2 is provided to the flow path P2. The detector D3 is provided to the flow path P3. The detector D4 is provided to the conversion unit U3. The detector D5 is provided to the flow path P4 and closer to the conversion unit U3 than the synthesis unit U5. The detector D7 is provided to the flow path P4 and closer to the synthesis unit U5 than the conversion unit U3. The detector D8 is provided to the flow path P6. The detector D9 is provided to the conversion unit U7. The number of detectors is not limited to the number of the detectors illustrated in FIG. 1 and the system only has to include at least one of the detectors D1 to D9. In FIG. 1, solid arrows indicate signals from the detectors to the integration controller CX.

[Emission Unit U0]

The emission unit U0 supplies a supply gas containing carbon dioxide to the recovery unit U1. The supply gas supplied from the emission unit U0 to the recovery unit U1 is not especially limited and may be, for example, effluent gas from power-generating facilities such as a thermal power station, a biomass power station, and the like or exhaust gas from industrial installations such as a steel factory, a cement factory, a chemical plant factory, a waste disposal factory, and the like. The supply gas is not limited to the exhaust gas but may be air in the atmosphere.

In the case where the emission unit U0 includes the controller C0, the controller C0 receives a control signal CS0 from the integration controller CX and controls the operating condition of the emission unit U0, for example, according to the control signal CS0. An example of a control target of the control signal CS0 can be a flow rate per unit time of the supply gas to be supplied from the emission unit U0 to the recovery unit U1.

[Recovery Unit U1]

The recovery unit U1 separates and recovers carbon dioxide ($CO_2$) from the supply gas supplied via the flow path P1 and thereby produces concentrated high-purity $CO_2$ gas. The high-purity $CO_2$ gas is introduced into the conversion unit U3 at the subsequent stage via the flow path P2.

The recovery unit U1 has, for example, a device such as a carbon dioxide chemical absorption device, a carbon dioxide physical adsorption and separation device, or a carbon dioxide membrane separation device.

Examples of the carbon dioxide chemical absorption device include a device that uses an amine solution as an absorbing liquid, makes the absorbing liquid absorb carbon dioxide in discharged gas, and then heats the absorbing liquid to separate and recover carbon dioxide from the absorbing liquid. In place of the amine solution, a solid absorbent with amine being a chemical absorbent supported on a porous support may be used to absorb carbon dioxide.

An example of the carbon dioxide physical adsorption and separation device can be a device that absorbs carbon dioxide or oxygen into an adsorbent such as zeolite or a molecular sieve, and changes the pressure or temperature to separate the main component or impurity component.

An example of the carbon dioxide membrane separation device can be a device that uses a separation membrane including activated carbon, a molecular sieve, or the like or a polymer membrane such as a molecular gate membrane, or the like to selectively separate and recover carbon dioxide.

The $CO_2$ purity of the high-purity $CO_2$ gas is not especially limited as long as it is higher than the $CO_2$ purity of the supply gas, and is preferably higher than 50% and 100% or lower and more preferably 90% or higher and 100% or lower. With a higher $CO_2$ purity of the high-purity $CO_2$ gas, the energy efficiency of a unit group at the subsequent stage can be further improved and the device size can be further reduced.

In the case where the recovery unit U1 includes the controller C1, the controller C1 receives a control signal CS1 from the integration controller CX and controls the operating condition of the recovery unit U1 according to the control signal CS1 to regulate the flow rate of the high-purity $CO_2$ gas. Examples of a control target by the controller C1 include a flow rate per unit time of the supply gas, a flow rate of the high-purity $CO_2$ gas, an amount of electric power to be input to the recovery unit U1, a heat quantity input to the recovery unit U1, the temperature of the absorbing liquid, the temperature of the adsorbent, the pressure condition at the $CO_2$ gas absorption and separation processes and so on. Examples of the controller C1 include a mass flow controller, a power supply, a temperature regulation heater, a pump, a compressor, and a variable throttle.

[Raw Material Supply Unit U2]

The raw material supply unit U2 supplies a first raw material to the conversion unit U3. The first raw material is accommodated, for example, in a tank.

Examples of the first raw material include water, water vapor, and hydrogen. A solution containing an electrolyte may be used as the first raw material. The solution containing the electrolyte includes solutions containing phosphate ion ($PO_4^{2-}$), borate ion ($BO_3^{3-}$), sodium ion ($Na^+$), potassium ion ($K^+$), calcium ion ($Ca^{2+}$), lithium ion ($Li^+$), cesium ion ($Cs^+$), magnesium ion ($Mg^{2+}$), chloride ion ($Cl^-$), hydrogen carbonate ion ($HCO_3^-$), carbonate ion ($CO_3^{2-}$), hydroxide ion ($OH^-$), and so on.

In the case where the raw material supply unit U2 includes the controller C2, the controller C2 receives a control signal CS2 from the integration controller CX and controls, for example, the flow rate of the first raw material to be supplied to the conversion unit U3. Examples of a control target by the controller C2 include a mass flow controller, a variable throttle, and so on.

[Conversion Unit U3]

The conversion unit U3 produces an intermediate compound from the high-purity $CO_2$ gas supplied from the recovery unit U1 and the first raw material supplied from the raw material supply unit U2. This electrochemically or thermochemically converts carbon dioxide into an intermediate compound. Examples of the intermediate compound include a carbon compound.

In the case of electrochemically converting carbon dioxide into the intermediate compound, the conversion unit U3 has an electrochemical reaction cell (electrolysis cell) and inputs electric power to an anode and a cathode in the electrolysis cell to convert carbon dioxide into the intermediate compound by electrolytic reaction. As a mode of the electrolysis cell, a solid polymer electrolyte cell or a solid-oxide electrolyte cell can be used.

Figure 2:
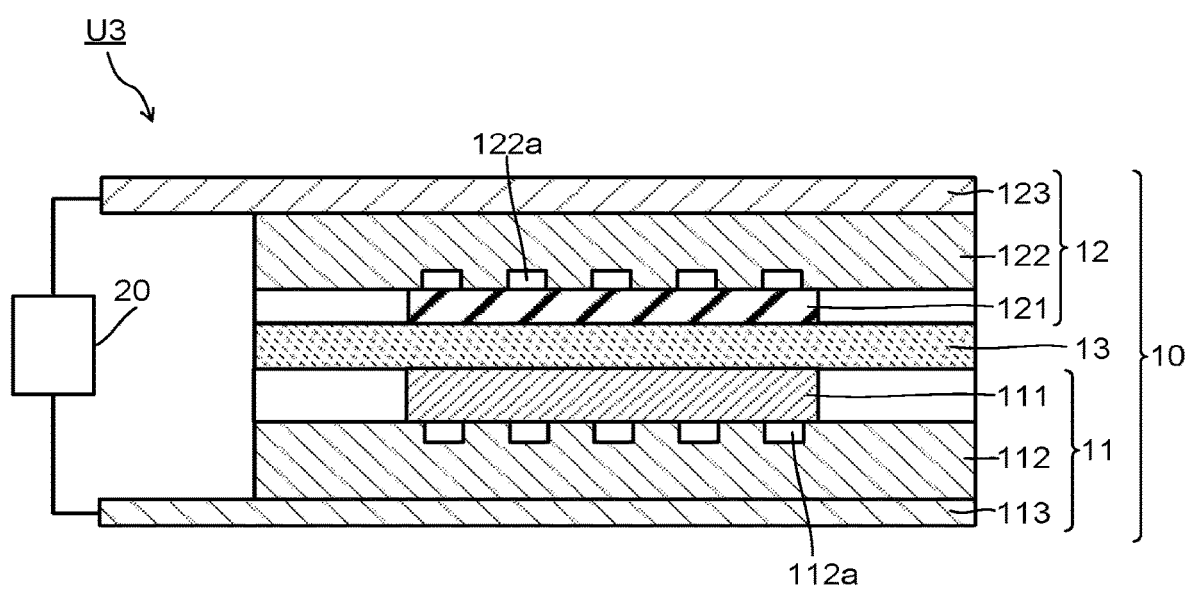
FIG. 2 is a schematic view for explaining a configuration example of the conversion unit U3.

FIG. 2 is a schematic view for explaining a configuration example of the conversion unit U3. FIG. 1 illustrates the conversion unit U3 including an electrolysis cell 10. The configuration of the conversion unit U3 is not limited to the configuration illustrated in FIG. 2.

The electrolysis cell 10 includes, an anode part 11, a cathode part 12, and a separator 13 separating the anode part 11 and the cathode part 12. The electrolysis cell 10 is, for example, sandwiched between a pair of support plates and fastened by bots or the like.

The anode part 11 includes an anode 111, an anode flow path 112a provided in a flow path plate 112, and an anode current collector 113.

The cathode part 12 includes a cathode 121, a cathode flow path 122a provided in a flow path plate 122, and a cathode current collector 123.

The anode 111 is an electrode (oxidation electrode) which activates an oxidation reaction of water ($H_2O$) in an anode solution to produce oxygen ($O_2$) and a hydrogen ion ($H^+$) or activates an oxidation reaction of a hydroxide ion ($OH^-$) produced in the cathode part 12 to produce oxygen and water.

The anode 111 is arranged between the separator 13 and the flow path plate 112 in a manner to be in contact with them. A first surface of the anode 111 is in contact with the separator 13. A second surface of the anode 111 is provided on the side opposite to the first surface of the anode 111 and faces the anode flow path 112a.

The compound to be produced by the oxidation reaction of the anode 111 differs depending on the kind of an oxidation catalyst or the like. In the case of using an electrolytic solution for the anode solution, the anode 111 can oxidize water ($H_2O$) to produce oxygen and hydrogen ion or oxidize a hydroxide ion ($OH^-$) to produce water and oxygen, and is preferably composed of mainly a catalyst material (anode catalyst material) capable of decreasing the overvoltage of the reaction. Examples of the catalyst material include metals such as platinum (Pt), palladium (Pd), nickel (Ni) and so on, alloys and intermetallic compounds containing those metals, binary metal oxides such as manganese oxide (Mn—O), iridium oxide (Ir—O), nickel oxide (Ni—O), cobalt oxide (Co—O), iron oxide (Fe—O), tin oxide (Sn—O), indium oxide (In—O), ruthenium oxide (Ru—O), lithium oxide (Li—O), lanthanum oxide (La—O), and so on, ternary metal oxides such as Ni—Co—O, Ni—Fe—O, La—Co—O, Ni—La—O, Sr—Fe—O, and so on, quaternary metal oxides such as Pb—Ru—Ir—O, La—Sr—Co—O, and so on, and metal complexes such as a Ru complex, a Fe complex, and so on.

The anode 111 preferably has a base member (carrier) having a structure capable of moving the anode solution and ions between the separator 13 and the anode flow path 112a, for example, a porous structure such as a mesh member, a punched member, or a porous member. Examples of the base member having the porous structure include those having relatively large voids such as a metal fiber sintered compact. The base member may be composed of a metal such as titanium (Ti), nickel (Ni), iron (Fe) or a metal material such as an alloy (for example, SUS) containing at least one of the metals, or may be composed of the aforementioned anode catalyst material. In the case of using the oxide as the anode catalyst material, it is preferable to form a catalyst layer by attaching or staking the anode catalyst material on the surface of the base member composed of the aforementioned metal material. The anode catalyst material preferably has a nanoparticle, a nanostructure, a nanowire or the like in order to enhance the oxidation reaction. The nanostructure is a structure obtained by forming nanoscale irregularities on the surface of the catalyst material. The oxidation catalyst does not always have to be provided at the oxidation electrode. An oxidation catalyst layer provided outside the oxidation electrode may be electrically connected to the oxidation electrode.

The cathode 121 is an electrode (reduction electrode) which activates a reduction reaction of carbon dioxide ($CO_2$) to produce an intermediate compound such as a carbon monoxide.

The cathode 121 is preferably composed of an ion conductive material in addition to an electrode substrate and a metal catalyst supported on a carbon material. The ion conductive material exhibits an action of transferring ions between metal catalysts contained in layers and thus exerts effects of enhancing the electrode activity.

As the ion conductive material, a cation exchange resin or an anion exchange resin is preferably used. These are polymers having ionic modifying groups and, known examples of the polymers include a cationic polymer having a perfluorosulfonic acid group. More specifically, a cation exchange resin such as Nafion (registered trademark) manufactured by Du Pont or Flemion (registered trademark) manufactured by AGC Inc., or an anion exchange resin such as DIAION (registered trademark) manufactured by Mitsubishi Chemical Corporation or Sustainion (registered trademark) manufactured by Dioxide Materials is used.

The carrier of the metal catalyst preferably has a porous structure. Examples of applicable material include carbon black such as ketjen black, Vulcan XC-72, activated carbon, carbon nanotube and so on in addition to the materials. The provision of the porous structure can increase the area of the active surface contributing to the oxidation-reduction reaction and thus can enhance the conversion efficiency.

It is preferable that not only the carrier but also the catalyst layer itself formed on the base member have the porous structure and have many relatively large voids. More specifically, it is preferable that the void distribution frequency becomes maximum in a range of a diameter of 5 μm or more and 200 μm or less in a pore size distribution of the catalyst layer measured by the mercury intrusion method. In this case, gas quickly diffuses in the whole catalyst layer and a reduction product becomes more likely to be discharged to the outside of the catalyst layer through the path, resulting in an electrode with high reaction efficiency.

To efficiently supply carbon dioxide to the catalyst layer, the electrode substrate supporting the catalyst layer preferably has a gas diffusion layer. The gas diffusion layer is formed of a conductive porous member. The gas diffusion layer formed of a water-repellent porous member is preferable because the amount of the water produced by the reduction reaction and the water moved from the oxidation side can be decreased, the water can be discharged via a reduction flow path, and the percentage of a carbon dioxide gas in the porous member can be made large.

An extremely small thickness of the gas diffusion layer is not preferable because the uniformity on the cell surface is degraded. On the other hand, an extremely large thickness is not preferable because the member cost increases and the efficiency is degraded due to the increase in diffusion resistance of gas. It is preferable to provide a denser diffusion layer (mesoporous layer) between the gas diffusion layer and the catalyst layer in order to further enhance the diffusibility because the denser diffusion layer changes the water repellency and the porous member degree to promote the diffusibility of gas and the discharge of a liquid component.

Examples of the metal catalyst supported on the carrier include materials of decreasing the activation energy for reducing the hydrogen ion and carbon dioxide. In other words, examples of the metal catalyst include metal materials of decreasing the overvoltage when producing the carbon compound by the reduction reaction of carbon dioxide. It is preferable to use, for example, at least one metal selected from the group consisting of gold (Au), silver (Ag), copper (Cu), platinum (Pt), palladium (Pd), nickel (Ni), cobalt (Co), iron (Fe), manganese (Mn), titanium (Ti), cadmium (Cd), zinc (Zn), indium (In), gallium (Ga), lead (Pb), and tin (Sn) and a metal oxide, or an alloy containing the metal. Not limited to these metals, a metal complex such as a ruthenium (Ru) complex or a rhenium (Re) complex may be used as the reduction catalyst. Further, a plurality of materials may be mixed. To the metal catalyst, various shapes such as a plate shape, a mesh shape, a wire shape, a particulate shape, a porous shape, a this-film shape, an island shape and so on can be applied.

In the case of applying a metal nanoparticle to the metal catalyst, its average diameter is preferably 1 nm or more and 15 nm or less, more preferably 1 nm or more and nm or less, furthermore preferably 1 nm or more and 5 nm or less. It is preferable to satisfy this condition because the surface area of metal per catalyst weight increases to exhibit high activity with a small amount of metal.

The anode 111 and the cathode 121 are connectable to a power supply 20. The power supply 20 may be provided outside the conversion unit U3. An example of the power supply 20 may be an ordinal commercial power supply or a battery, or an electric power source of converting renewable energy into electric energy and supplying it. Examples of electric power include electric power obtained by converting kinetic energy or potential energy such as wind power, water power, geothermal power or tidal power into electric energy, electric power produced by a solar cell having a photoelectric conversion element of converting light energy into electric energy, electric power produced by a fuel cell or a storage battery of converting chemical energy into electric energy, and electric power obtained by a device of converting vibrational energy such as sound into electric energy.

The anode flow path 112a has a function of supplying, to the anode 111, the first raw material supplied from the raw material supply unit U2 via the flow path P3.

The anode flow path 112a is composed of a pit (groove/recess) provided in the flow path plate 112. The flow path plate 112 has an inlet port and an outlet port (none of them is illustrated) connected to the anode flow path 112a, so that the raw material is introduced and discharged by a pump (not illustrated) via the inlet port and the outlet port.

The material of the flow path plate 112 includes, for example, a material having low chemical reactivity and having no conductivity. Examples of the material include insulating resin materials such as an acrylic resin, polyetheretherketone (PEEK), a fluorocarbon resin, and so on. The flow path plate 112 has a not-illustrated screw hole for fastening. Further, the flow path plate 112 is mainly formed of one member, and may be formed of different members and constituted by stacking them one on the other. Further, functions of hydrophilicity and repellancy may be given to the flow path plate 112 by performing surface treatment on a part or the whole thereof.

The cathode flow path 122a faces the first surface of the cathode 121. The cathode flow path 122a has a function of supplying, to the cathode 121, the high-purity $CO_2$ gas to be supplied from the recovery unit U1 via the flow path P2. To the cathode 121, not only the high-purity $CO_2$ gas but also water vapor can be supplied.

The cathode flow path 122a is composed of a pit (groove/recess) provided in the flow path plate 122. The flow path plate 122 has an inlet port and an outlet port (none of them is illustrated) connected to the cathode flow path 122a, so that the gas is introduced and discharged by a pump (not illustrated) via the inlet port and the outlet port.

It is preferable to use, as the material of the flow path plate 122, a material having low chemical reactivity and having high conductivity. Examples of the material include metal materials such as Ti and SUS, and carbon. The flow path plate 122 has not-illustrated inflow port and outflow port of the cathode flow path 122a and screw hole for fastening. Further, in front and rear of each flow path plate, not-illustrated packing is sandwiched according to the need. Further, the flow path plate 122 is mainly formed of one member, and may be formed and constituted of different members and constituted by stacking them one on the other. Further, functions of hydrophilicity and repellancy may be given to the flow path plate 122 by performing surface treatment on a part or the whole thereof.

The flow path plate 122 can include a land in contact with the cathode 121 for electrical connection with the cathode 121. Examples of the shape of the cathode flow path 122a include shapes such as a shape adjacent to a columnar land, a serpentine shape made by folding an elongated flow path, and so on, and the shape is not especially limited as long as the shape has a cavity. It is preferable to constitute the cathode flow path 122a by combination of a plurality of flow paths or serpentine flow paths connected in parallel because the uniformity of gas to be supplied to the cathode 121 can be enhanced and the uniformity of the electrolytic reaction can be enhanced.

The intermediate compound produced by the reduction reaction defers depending on the kind of a metal catalyst functioning as the reduction catalyst. Examples of the intermediate compound produced by the reduction reaction include carbon compounds such as carbon monoxide (CO), formic acid (HCOOH), methane ($CH_4$), methanol ($CH_3OH$), ethane ($C_2H_6$), ethylene ($C_2H_4$), ethanol ($C_2H_5OH$), formaldehyde (HCHO), and ethylene glycol. Further, simultaneously with the conversion of carbon dioxide, hydrogen may be produced as a side reaction. At the anode 111, there occurs a reaction of producing oxygen from water or water vapor.

The substances produced at the cathode 121 and the anode 111 in the electrolysis cell 10 and unreacted raw material are individually discharged from the conversion unit U3. The substance produced at the cathode 121 of them is supplied to the synthesis unit U5 at the subsequent stage via the flow path P4. In the middle of the flow path P4, a gas regulation unit can be provided for regulating the components in the gas to be supplied from the conversion unit U3 to a gas component ratio suitable for the synthesis condition in the synthesis unit U5.

In the electrochemical reaction in the electrolysis cell 10, part of the high-purity $CO_2$ gas supplied to the cathode 121 moves to the anode 111, and the exhaust component from the anode flow path 112a may contain carbon dioxide. In this case, the carbon dioxide in the exhaust component discharged from the conversion unit U3 via the flow path P5 can be separated and recovered, and the recovered carbon dioxide gas can be supplied again to the conversion unit U3 and used as a carbon dioxide raw material. In this event, the device performing separation and recovery may be the recovery unit U1, or another recovery unit may be provided at the stage subsequent to the conversion unit U3.

In the case of thermochemically converting carbon dioxide into the intermediate compound in the conversion unit U3, the conversion unit U3 includes a reactor, supplies the high-purity $CO_2$ gas from the recovery unit U1 and hydrogen from the raw material supply unit U2 to the reactor, and inputs thermal energy thereto to convert carbon dioxide into the intermediate compound by a reverse shift reaction. The reverse shift reaction can be expressed by Expression (1).

$$CO_2 + H_2 \rightarrow CO + H_2O \tag{1}$$

The reactor includes a catalyst efficiently causing the reaction of Expression (1) and causes the reaction of Expression (1) at predetermined temperature and pressure. The reaction temperature is preferably 600° C. or higher and 1000° C. or lower, and the pressure is preferably 1 atm or higher and 10 atm or lower. The produced gas and the unreacted raw material discharged from the reactor are supplied to the synthesis unit U5 at the subsequent stage.

In the case where the conversion unit U3 has the controller C3, the controller C3 receives a control signal CS3 from the integration controller CX, and controls the flow rate per unit time of the intermediate compound to be supplied to the synthesis unit U5 at the subsequent stage by controlling the operation condition of the conversion unit U3. In the case of the conversion unit U3 which electrochemically converts carbon dioxide into the intermediate compound, examples of the controller C3 include a power supply to be input to the electrolysis cell, a flowmeter which regulates the flow rate per unit time of carbon dioxide and the first raw material to be supplied to the electrolysis cell, a controller which controls the temperature and pressure of the electrolysis cell, and so on. In the case of the conversion unit U3 which thermochemically converts carbon dioxide into the intermediate compound, examples of the controller C3 include a thermometer which measures the temperature in the reactor, a hygrometer which measures the humidity in the reactor, a pressure controller which controls the pressure in the reactor, a flowmeter which measures the flow rate per unit time of carbon dioxide and hydrogen to be supplied to the reactor, and so on.

[Raw Material Supply Unit U4]

The raw material supply unit U4 supplies a second raw material as needed to the synthesis unit U5 via the flow path P4. FIG. 1 illustrates the raw material supply unit U4 connected to the flow path P4 but not limited to this. Examples of the second raw material include carbon monoxide, and hydrogen. The raw material supply unit U4 does not always has to be provided.

In the case where the raw material supply unit U4 includes the controller C4, the controller C4 receives a control signal CS4 from the integration controller CX, and controls the supply rate of the second raw material. Examples of a control target by the controller C4 include a mass flow controller and a variable throttle.

[Synthesis Unit U5]

The synthesis unit U5 synthesizes a carbon compound using the intermediate compound from the conversion unit U3. In the case of providing the raw material supply unit U4, the carbon compound can be synthesized by also supplying the second raw material from the raw material supply unit U4 to the synthesis unit U5.

The synthesis unit U5 has a reactor. The synthesis reaction by the reactor includes reactions such as a chemical reaction, an electrochemical reaction, a biological conversion reaction using organisms such as algae, enzyme, yeast, bacteria and so on. An example of the synthesis by the chemical reaction is a synthesis by a synthetic fuel from carbon monoxide and hydrogen by Fischer-Tropsch process expressed by Expression (2).

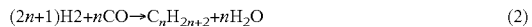

$$(2n+1)H_2 + nCO \rightarrow C_nH_{2n+2} + nH_2O \quad (2)$$

In this case, gas containing carbon monoxide and hydrogen is supplied from the conversion unit U3 to the synthesis unit U5 to cause the reaction in Expression (2), and the composition ratio between carbon monoxide and hydrogen is not be suitable for the reaction in Expression (2) in some cases. In this case, the raw material supply unit U4 is provided, and carbon monoxide and hydrogen are complementarily supplied from the raw material supply unit U4 to the synthesis unit U5 via the flow path P4 in order to maximize the synthesis reaction by the component ratio between carbon monoxide and hydrogen.

In the chemical reaction, the electrochemical reaction, the biological conversion of bacteria or the like, at least one of parameters such as the reaction efficiency and reaction speed may improve when the temperature is higher than room temperature. When the temperature of the raw material gas to be introduced into the synthesis unit U5 is set to 60° C. or higher and 300° C. or lower, the energy conversion efficiency of the synthesis unit U5 can be enhanced. The biological conversion reaction of bacteria or the like proceeds most efficiently near 80° C., so that when the reduction product is supplied at a temperature of 60° C. or higher and 100° C. or lower to the synthesis unit U5, the efficiency further improves. In order to improve the reaction efficiency of the synthesis unit U5, energy may be applied from the outside to increase the temperature or apply pressure.

Examples of the carbon compound to be obtained from the synthesis reaction by the synthesis unit U5 include a hydrocarbon-based fuel such as a jet fuel, diesel, and gasoline, alcohols such as methanol, ethanol, and butanol, and phosgene being a raw material of isocyanates. These carbon compounds are preferably high-purity carbon compounds at synthesis, and the synthesis by the synthesis unit U5 can include distillation and production processes.

The raw material gas such as carbon monoxide is used with a reducing agent in the synthesis unit U5 to produce carbon dioxide as a result of the reaction in some cases. In this case, the produced carbon dioxide is separated and recovered and supplied again to the conversion unit U3, thereby enabling constitution of a system with improved utilization ratio of substances.

As a result of the synthesis reaction in the synthesis unit U5, unreacted raw material gas is discharged in some cases. The unreacted raw material gas contains, for example, carbon dioxide. The unreacted raw material gas may contain an intermediate compound such as carbon monoxide. In this case, the unreacted raw material gas is recovered and supplied to one of the recovery unit U1, the conversion unit U3, and the synthesis unit U5, thereby enabling constitution of a system with high utilization ratio of raw materials.

In the case where the synthesis unit U5 include a controller C5, the controller C5 receives a control signal CS5 from the integration controller CX, and controls the operating condition of the synthesis unit U5 to regulate the amount (mass, volume, concentration or the like) of the carbon compound to be manufactured. Examples of a control targets by the controller C5 include a regulator which controls the reaction temperature and the pressure condition at the synthesis of the carbon compound, an electric power regulator when operating the synthesis unit U5, and so on.

The synthesis unit U5 illustrated in FIG. 1 illustrates an example of discharging a mixture (first mixture) containing a target carbon compound as a main component via the flow path P6, and discharging another mixture (second mixture) via the flow path P7 but not limited to this. The other mixture may contain a carbon compound other than the carbon compound contained in the first mixture.

[Detectors D1 to D9]

Each detector detects a parameter such as a component amount or the like of fluid flowing through a corresponding flow path or unit, generates a data signal being a detection signal, and transmits the data signal to the integration controller CX. The transmission method of the data signal may be a wired method or a wireless method.

Each detector may be an analyzer or a concentration meter which measures the concentration of at least one of gas or liquid, a flowmeter which measures the flow rate per unit time of at least one of gas or liquid, or a combination of them. Further, each detector may include a measuring meter which measures the mass or volume of an object. In the case of using the analyzer as each detector, a device such as gas chromatography, a high-performance liquid chromatography, an ion chromatography capable of analyzing the hydrocarbon in the gas or liquid. In the case of using the concentration meter as the detector, a non dispersive infrared (NDIR) gas sensor or a semiconductor gas sensor may be used.

The detector D1 generates a data signal DS1. The data signal DS1 includes data, for example, indicating the flow rate per unit time of the supply gas to be supplied to the recovery unit U1 (flow rate per unit time of the supply gas contained in the fluid flowing through the flow path P1).

The detector D2 generates a data signal DS2. The data signal DS2 includes, for example, data indicating the flow rate per unit time of carbon dioxide contained in the fluid flowing through the flow path P2.

The detector D3 generates a data signal DS3. The data signal DS3 includes, for example, data indicating the flow rate per unit time of the first raw material contained in the fluid flowing through the flow path P3.

The detector D4 generates a data signal DS4. The data signal DS4 includes, for example, data indicating the voltage to be applied to the conversion unit U3 and the amount of current to be supplied. For example, in the case where the conversion unit U3 of electrochemically converting carbon dioxide into the intermediate compound has the detector D4, an ammeter and a voltmeter which detect flowing current and voltage between the anode 111 and the cathode 121 of the electrolysis cell 10 may be used as the examples of the detector D4.

The detector D5 generates a data signal DS5. The data signal DS5 includes, for example, data indicating the flow rate per unit time of the intermediate compound contained in the fluid flowing on the conversion unit U3 side of the flow path P4 (a region between a connection point between the flow path P4 and the raw material supply unit U4, and, the conversion unit U3).

The detector D6 generates a data signal DS6. The data signal DS6 includes, for example, data indicating the flow rate per unit time of substances contained in the fluid flowing through the flow path P5.

The detector D7 generates a data signal DS7. The data signal DS7 includes, for example, data indicating the total flow rate per unit time of the intermediate compound and the second raw material contained in the fluid flowing on the synthesis unit U5 side of the flow path P4 (a region between a connection point between the flow path P4 and the raw material supply unit U4, and, the synthesis unit U5).

The detector D8 generates a data signal DS8. The data signal DS8 includes, for example, data indicating the flow rate per unit time and concentration of at least one substance contained in the fluid flowing through the flow path P6, and the temperature and the pressure of the fluid.

The detector D9 generates a data signal DS9. The data signal DS9 includes, for example, data indicating the flow rate and concentration per unit time of at least one substance contained in the fluid flowing through the flow path P7, and the temperature and the pressure of the fluid.

[Integration Controller CX]

The integration controller CX is electrically connected to the detectors and the controllers. The integration controller CX has a reception part CX1 which receives a detection signal (data signal) including measured data from each detector, a calculation part CX2 which collates the measured data with predetermined plan data and generates a control signal by calculation processing (simulation) according to a collation result, and a transmission part CX3 which receives a control signal from the calculation part CX2 and outputs the control signal to a corresponding controller in accordance with the reception of the control signal. In FIG. 1, arrows of dotted lines represent signals from the integration controller CX to the controllers.

The value of the plan data is set in advance in accordance with an operation plan or a production plan of The system. The calculation part CX2 stores in advance request criteria (numerical range) of the measured value (data signal) transmitted from each detector, for example, a request criteria range of a difference between the inflow rate of the supply gas into the recovery unit U1 actually measured by the detector and a predetermined inflow rate in accordance with the plan data, a control signal is generated in the calculation part in accordance with the relation between the request criteria range and the measured value, and the control signal is output from the transmission part to the controller. The calculation part CX2 is composed of, for example, hardware such as a personal computer (PC) or microcomputer including a program and simulation software. The operation is held as an operating program in advance in a computer-readable recording medium such as a memory, and the operation may be executed by reading the operating program stored in the recording medium by the hardware when needed. The plan data may be held in the recording medium.

(Example of a Method of Controlling the System)

Next, an example of the method of controlling the system illustrated in FIG. 1 will be explained below. FIG. 3 is a flowchart for explaining the method example of controlling the system and illustrates an example of the operation relating to the integration controller CX at a plurality of steps.

First of all, each detector measures the amount of each substance contained in the fluid flowing through the arranged flow path and generates a data signal (detection signal) including the measured data (S1).

Next, each detector transmits the data signal in accordance with the measured value of the parameter such as the amount of each object to the integration controller CX (S2).

Then, the reception part CX1 of the integration controller CX receives the data signal from each detector (S3). Each received data signal is input to the calculation part CX2 of the integration controller CX.

Then, the calculation part CX2 collates the measured data included in each received data signal with the plan data corresponding to each data signal stored in the integration controller CX (S4).

When it is determined that the value of the measured data is within the request criteria range of the value of the plan data by the collation (S4 No), the flow returns again to the measurement step (S1), and each detector measures the parameter of each object. When it is determined that the value of the measured data is outside the request criteria range of the value of the plan data by the collation (S4 Yes), the calculation part CX2 generates a control signal for controlling the operation condition of each unit so that the parameter of each object falls within the request criteria range of the value of the plan data (S5). The generated control signal is transmitted from the transmission part CX3 to the controller of a corresponding unit (S6).

The corresponding units receive the control signals and execute the operations on the operation conditions in accordance with the received control signals (S7). Then, each detector measures the parameter of each object such as a substance amount flowing through the arranged flow path similarly to the measurement step (S1) (S8). Thus, verification by the control signal is executed. The above is the explanation of the method example of controlling the system.

The system according to the embodiment can integrally control the plurality of units by using the integration controller CX and can achieve the operation autonomously controlled in the system, for example, even when a deviation in substance amount of the raw material or the like occurs among the units.

A conventional carbon compound manufacturing system individually performs adjustment in each unit when the deviation in substance amount of the raw material or the like occurs among the units. The conventional carbon compound manufacturing system needs a buffer tank connected to each flow path in order to eliminate the deviation. The buffer tank is connected to each flow path and temporarily accommodates the fluid flowing through each flow path therein, and thereby can adjust the flow rate or the like. However, the buffer tank causes a cost increase of the system such as an increase in plant construction cost.

In contrast to the above, the system in the embodiment does not have to be provided with any buffer tanks connected to each flow path. Since no buffer tank is provided, the plant construction cost can be saved and the system can be manufacture at low cost. Further, it is possible to provide a carbon compound manufacturing system with decreased plant area and increased utilization efficiency of the raw material.

Here, concrete control examples of the system will be explained. Each control example will be explained assuming that the intermediate compound is carbon monoxide. The control example of the system is not limited to the following control examples.

First Control Example

A control example, for example, in the case of operating the conversion unit U3 with electric power by the renewable energy and when the value of the electric power input to the conversion unit U3 increases to be larger than a desired value in the system illustrated in FIG. 1 will be explained.

First, the detector D4 measures the electric power input to the conversion unit U3 by measuring the voltage and current supplied to the conversion unit U3 and generating the data signal DS4 (S1).

Next, the detector D4 transmits the data signal DS4 including the measured data on the electric power to the integration controller CX (S2).

Then, the reception part CX1 of the integration controller CX receives the data signal DS4 from the detector D4 (S3). The received data signal DS4 is input to the calculation part CX2 via the reception part CX1 of the integration controller CX.

Then, the calculation part CX2 collates the measured data included in the received data signal DS4 with the plan data corresponding to the data signal DS4 stored in the integration controller CX (S4).

This collation enables the value of the measured data to be determined to be larger than the request criteria range of the value of the plan data (S4 Yes), and the calculation part CX2 generates the control signal CS0, the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7).

The controller C0 of the emission unit U0 adjusts, in accordance with the control signal CS0, the operation condition of the emission unit U0 so as to increase the amount of the supply gas to be supplied to the recovery unit U1 as compared with that at the measurement step (S1).

The controller C1 of the recovery unit U1 adjusts, in accordance with the control signal CS1, the operation condition of the recovery unit U1 so as to increase the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to increase the conversion amount of carbon dioxide by the conversion unit U3 as compared with that at the measurement step (S1).

The controller C4 of the raw material supply unit U4 adjusts, in accordance with the control signal CS4, the operation condition of the raw material supply unit U4 so as to decrease the amount of carbon monoxide to be supplied to the synthesis unit U5 via the flow path P4 as compared with that at the measurement step (S1). Thus, the amount of the intermediate compound to be supplied to the synthesis unit U5 is held within the same range as that at the measurement step (S1).

The controller C5 of the synthesis unit U5 operates the synthesis unit U5 in accordance with the control signal CS5 on the same operation condition as that at the measurement step (S1).

Thereafter, each detector measures the parameter of the object similarly to the measurement step (S1) (S8). Thus, the operation status after the adjustment is verified. The detector D7 measures the amount of carbon monoxide flowing on the synthesis unit U5 side of the flow path P4 and generates the data signal DS7.

In the first control example, even in the case where the electric power increases, the synthesis unit U5 synthesizes the carbon compound while the amount of the intermediate compound to be supplied to the synthesis unit U5 is controlled within a fixed range. This can suppress the fluctuation in synthetic amount of the carbon compound due to the deviation in substance amount among the units without using a buffer tank.

In the first control example, the controller C2, the detector D1, the detector D2, the detector D3, the detector D5, the detector D6, the detector D8 and the detector D9 do not always have to be operated. In the case of operating those components, the controller C2 and the detectors D1, D2, D3, D5, D6, D8, D9 each measure the parameter of the object at each part, so that when the measured data is determined to be abnormal in the integration controller CX, each part may be controlled so as to be brought into a normal state. For example, in the case of operating the controller C2, for example, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Second Control Example

A control example, for example, in the case of operating the conversion unit U3 with electric power by the renewable energy and when the value of the electric power input to the conversion unit U3 decreases to be smaller than a desired value in the system illustrated in FIG. 1 will be explained.

First, the detector D4 detects the electric power to be input to the conversion unit U3 by measuring the voltage and current supplied to the conversion unit U3 and generating the data signal DS4 (S1).

Next, the detector D4 transmits the data signal DS4 including the measured data on the electric power to the integration controller CX (S2).

Then, the reception part CX1 of the integration controller CX receives the data signal DS4 from the detector D4 (S3). The received data signal DS4 is input to the calculation part CX2 via the reception part CX1 of the integration controller CX.

Then, the calculation part CX2 collates the measured data included in the received data signal DS4 with the plan data corresponding to the data signal DS4 stored in the integration controller CX (S4).

This collation enables the value of the measured data to be determined to be smaller than the request criteria range of the value of the plan data (S4 Yes), and the calculation part CX2 generates the control signal CS0, the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7).

The controller C0 of the emission unit U0 adjusts, in accordance with the control signal CS0, the operation condition of the emission unit U0 so as to decrease the amount of the supply gas to be supplied to the recovery unit U1 as compared with that at the measurement step (S1).

The controller C1 of the recovery unit U1 adjusts, in accordance with the control signal CS1 the operation condition of the recovery unit U1 so as to decrease the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to decrease the conversion amount of carbon dioxide by the conversion unit U3 as compared with that at the measurement step (S1).

The controller C4 of the raw material supply unit U4 adjusts, in accordance with the control signal CS4, the operation condition of the raw material supply unit U4 so as to increase the flow rate of carbon monoxide to be supplied to the synthesis unit U5 via the flow path P4 as compared with that at the measurement step (S1). Thus, the amount of the intermediate compound to be supplied to the synthesis unit U5 is held within the same range as that at the measurement step (S1).

The controller C5 of the synthesis unit U5 operates, in accordance with the control signal CS5, the synthesis unit U5 on the same operation condition as that at the measurement step (S1).

Thereafter, each detector measures the parameter of the object similarly to the measurement step (S1) (S8). Thus, the operation status after the adjustment is verified. The detector D7 measures the amount of carbon monoxide flowing on the synthesis unit U5 side of the flow path P4 and generates the data signal DS7.

In the second control example, even in the case where the electric power decreases, the synthesis unit U5 synthesizes the carbon compound while the amount of the intermediate compound to be supplied to the synthesis unit U5 is controlled within a fixed range. This can suppress the fluctuation in synthetic amount of the carbon compound due to the deviation in substance amount among the units without using a buffer tank.

In the second control example, the controller C2, the detector D1, the detector D2, the detector D3, the detector D5, the detector D6, the detector D8 and the detector D9 do not always have to be operated. In the case of operating those components, the controller C2 and the detectors D1, D2, D3, D5, D6, D8, D9 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Third Control Example

Another control example, for example, in the case of operating the conversion unit U3 with electric power by the renewable energy and when the value of the electric power to be input to the conversion unit U3 increases to be larger than a desired value in the system illustrated in FIG. 1 will be explained.

First, the detector D4 detects the electric power to be input to the conversion unit U3 by measuring the voltage and current supplied to the conversion unit U3 (S1).

Next, the detector D4 transmits the data signal DS4 including the measured data on the electric power to the integration controller CX (S2).

Then, the reception part CX1 of the integration controller CX receives the data signal DS4 from the detector D4 (S3). The received data signal DS4 is input to the calculation part CX2 via the reception part CX1 of the integration controller CX.

Then, the calculation part CX2 collates the measured data included in the received data signal DS4 with the plan data corresponding to the data signal DS4 stored in the integration controller CX (S4).

This collation enables the value of the measured data to be determined to be larger than the request criteria range of the value of the plan data (S4 Yes), and the calculation part CX2 generates the control signal CS0, the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7). Then, each detector measures the parameter of the object similarly to the measurement step (S1) (S8). Thus, verification by the control signal is executed.

The controller C0 of the emission unit U0 adjusts, in accordance with the control signal CS0, the operation condition of the emission unit U0 so as to increase the amount of the supply gas to be supplied to the recovery unit U1 as compared with that at the measurement step (S1).

The controller C1 of the recovery unit U1 adjusts, in accordance with the control signal CS1, the operation condition of the recovery unit U1 so as to increase the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to increase the conversion amount of carbon dioxide by the conversion unit U3 as compared with that at the measurement step (S1).

The controller C4 of the raw material supply unit U4 adjusts, in accordance with the control signal CS4, the operation condition of the raw material supply unit U4 so as to increase the flow rate of hydrogen to be supplied to the synthesis unit U5 via the flow path P4 as compared with that at the measurement step (S1).

The controller C5 of the synthesis unit U5 adjusts, in accordance with the control signal CS5, the operation condition of the synthesis unit U5 so as to increase the amount of the carbon compound to be synthesized as compared with that at the measurement step (S1). Thus, the amounts of the carbon compound to be discharged via the flow path P6 and the carbon compound to be discharged via the flow path P7 increase but the component ratio is kept constant.

Then, each detector measures the parameter of the object similarly to the measurement step (S1) (S8). Thus, the operation status after the adjustment is verified. The detector D8 measures the amount of the carbon compound flowing through the flow path P6 and generates the data signal DS8. The detector D9 measures the amount of the carbon compound flowing through the flow path P7 and generates the data signal DS9.

In the third control example, even in the case where the electric power increases, the component ratio of the carbon compound to be synthesized by the synthesis unit U5 is controlled within a fixed range. This can suppress the fluctuation in synthetic amount of the carbon compound due to the deviation in substance amount among the units without using a buffer tank.

In the third control example, the controller C2, the detector D1, the detector D2, the detector D3, the detector D5, the detector D6, and the detector D7 do not always have to be operated. In the case of operating those components, the controller C2 and the detectors D1, D2, D3, D5, D6, D7 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Fourth Control Example

Another control example, for example, in the case of operating the conversion unit U3 with electric power by the renewable energy and when the value of the electric power to be input to the conversion unit U3 decreases to be smaller than a desired value in the system illustrated in FIG. 1 will be explained.

First, the detector D4 detects the electric power to be input to the conversion unit U3 by measuring the voltage and current supplied to the conversion unit U3 and generating the data signal DS4 (S1).

Next, the detector D4 transmits the data signal DS4 including the measured data on the electric power to the integration controller CX (S2).

Then, the reception part CX1 of the integration controller CX receives the data signal DS4 from the detector D4 (S3). The received data signal DS4 is input to the calculation part CX2 via the reception part CX1 of the integration controller CX.

Then, the calculation part CX2 collates the measured data included in the received data signal DS4 with the plan data corresponding to the data signal DS4 stored in the integration controller CX (S4).

This collation enables the value of the measured data to be determined to be smaller than the request criteria range of the value of the plan data (S4 Yes), and the calculation part CX2 generates the control signal CS0, the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7).

The controller C0 of the emission unit U0 adjusts, in accordance with the control signal CS0, the operation condition of the emission unit U0 so as to decrease the amount of the supply gas to be supplied to the recovery unit U1 as compared with that at the measurement step (S1).

The controller C1 of the recovery unit U1 adjusts, in accordance with the control signal CS1, the operation condition of the recovery unit U1 so as to decrease the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to decrease the conversion amount of carbon dioxide by the conversion unit U3 as compared with that at the measurement step (S1).

The controller C4 of the raw material supply unit U4 adjusts, in accordance with the control signal CS4, the operation condition of the raw material supply unit U4 so as to decrease the amount of hydrogen to be supplied to the synthesis unit U5 via the flow path P4 as compared with that at the measurement step (S1).

The controller C5 of the synthesis unit U5 adjusts, in accordance with the control signal CS5, the operation condition of the synthesis unit U5 so as to decrease the amount of the carbon compound to be synthesized as compared with that at the measurement step (S1). Thus, the amounts of the carbon compound to be discharged via the flow path P6 and the carbon compound to be discharged via the flow path P7 increase but the component ratio is kept constant.

Then, each detector measures the parameter of the object similarly to the measurement step (S1) (S8). Thus, the operation status after the adjustment is verified. The detector D8 measures the amount of the carbon compound flowing through the flow path P6 and generates the data signal DS8. The detector D9 measures the amount of the carbon compound flowing through the flow path P7 and generates the data signal DS9.

In the fourth control example, even in the case where the electric power decreases, the component ratio of the carbon compound to be synthesized by the synthesis unit U5 is controlled within a fixed range. This can suppress the fluctuation in synthetic amount of the carbon compound due to the deviation in substance amount among the units without using a buffer tank.

In the fourth control example, the controller C2, the detector D1, the detector D2, the detector D3, the detector D5, the detector D6, and the detector D7 do not always have to be operated. In the case of operating those components, the controller C2 and the detectors D1, D2, D3, D5, D6, D7 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Fifth Control Example

A control example when the amount of the supply gas supplied from the emission unit U0 to the recovery unit U1 increases to be larger than a desired value in the system illustrated in FIG. 1 will be explained.

First, the detector D1 measures the flow rate of the supply gas supplied to the recovery unit U1 and generates the data signal DS1 (S1).

Next, the detector D1 transmits the data signal DS1 including the measured data on the flow rate of the supply gas to the integration controller CX (S2).

Then, the reception part CX1 of the integration controller CX receives the data signal DS1 from the detector D1 (S3). The received data signal DS1 is input to the calculation part CX2 via the reception part CX1 of the integration controller CX.

Then, the calculation part CX2 collates the measured data included in the received data signal DS1 with the plan data corresponding to the data signal DS1 stored in the integration controller CX (S4).

This collation enables the value of the measured data to be determined to be larger than the request criteria range of the value of the plan data (S4 Yes), and the calculation part CX2 generates the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7).

The controller C1 of the recovery unit U1 adjusts, in accordance with the control signal CS1, the operation condition of the recovery unit U1 so as to increase the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to increase the amount of electric power to be supplied to the conversion unit U3 as compared with that at the measurement step (S1).

The controller C4 of the raw material supply unit U4 adjusts, in accordance with the control signal CS4, the operation condition of the raw material supply unit U4 so as to decrease the flow rate of carbon monoxide to be supplied to the synthesis unit U5 via the flow path P4 as compared with that at the measurement step (S1). Thus, the amount of the intermediate compound to be supplied to the synthesis unit U5 is held within the same range as that at the measurement step (S1).

The controller C5 of the synthesis unit U5 operates, in accordance with the control signal CS5, the synthesis unit U5 on the same operation condition as that at the measurement step (S1).

Thereafter, each detector measures the parameter of the object similarly to the measurement step (S1) (S8). Thus, the operation status after the adjustment is verified. The detector D7 measures the flow rate of carbon monoxide flowing on the synthesis unit U5 side of the flow path P4 and generates the data signal DS7.

In the fifth control example, even in the case where the amount of the supply gas increases, the synthesis unit U5 synthesizes the carbon compound while the amount of the intermediate compound to be supplied to the synthesis unit U5 is controlled within a fixed range. This can suppress the fluctuation in synthetic amount of the carbon compound due to the deviation in substance amount among the units without using a buffer tank.

In the fifth control example, the controller C0, the controller C2, the detector D2, the detector D3, the detector D5, the detector D6, the detector D8 and the detector D9 do not always have to be operated. In the case of operating those components, the controller C0, the controller C2, and the detectors D2, D3, D5, D6, D8, D9 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Sixth Control Example

A control example when the amount of the supply gas supplied from the emission unit U0 to the recovery unit U1 decreases to be smaller than a desired value in the system illustrated in FIG. 1 will be explained.

First, the detector D1 measures the flow rate of the supply gas supplied to the recovery unit U1 and generates the data signal DS1 (S1).

Next, the detector D1 transmits the data signal DS1 including the measured data on the flow rate of the supply gas to the integration controller CX (S2).

Then, the reception part CX1 of the integration controller CX receives the data signal DS1 from the detector D1 (S3). The received data signal DS1 is input to the calculation part CX2 via the reception part CX1 of the integration controller CX.

Then, the calculation part CX2 collates the measured data included in the received data signal DS1 with the plan data corresponding to the data signal DS1 stored in the integration controller CX (S4).

This collation enables the value of the measured data to be determined to be larger than the request criteria range of the value of the plan data (S4 Yes), and the calculation part CX2 generates the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute the operations on the operation conditions in accordance with the received control signals (S7). Then, each detector measures the parameter of the object similarly to the measurement step (S1) (S8). Thus, verification by the control signal is executed.

The controller C1 of the recovery unit U1 adjusts, in accordance with the control signal CS1, the operation condition of the recovery unit U1 so as to decrease the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to decrease the amount of electric power to be supplied to the conversion unit U3 as compared with that at the measurement step (S1).

The controller C4 of the raw material supply unit U4 adjusts, in accordance with the control signal CS4, the operation condition of the raw material supply unit U4 so as to increase the amount of carbon monoxide and the flow rate of hydrogen to be supplied to the synthesis unit U5 via the flow path P4 as compared with those at the measurement step (S1). Thus, the amount of the intermediate compound to be supplied to the synthesis unit U5 is held within the same range as that at the measurement step (S1).

The controller C5 of the synthesis unit U5 operates, in accordance with the control signal CS5, the synthesis unit U5 on the same operation condition as that at the measurement step (S1).

Thereafter, each detector measures the parameter of the object similarly to the measurement step (S1) (S8). Thus, the operation status after the adjustment is verified.

In the sixth control example, even in the case where the amount of the supply gas decreases, the synthesis unit U5 synthesizes the carbon compound while the amount of the intermediate compound to be supplied to the synthesis unit U5 is controlled within a fixed range. This can suppress the fluctuation in synthetic amount of the carbon compound due to the deviation in substance amount among the units without using a buffer tank.

In the sixth control example, the controller C0, the controller C2, the detector D2, the detector D3, the detector D4, the detector D5, the detector D6, the detector D7, the detector D8 and the detector D9 do not always have to be operated. In the case of operating those components, the controller C0, the controller C2, and the detectors D2, D3, D4, D5, D6, D7, D8, D9 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Seventh Control Example

Another control example when the amount of the supply gas to be supplied from the emission unit U0 to the recovery unit U1 increases to be larger than a desired value in the system illustrated in FIG. 1 will be explained.

First, the detector D1 measures the flow rate of the supply gas supplied to the recovery unit U1 and generates the data signal DS1 (S1).

Next, the detector D1 transmits the data signal DS1 including the measured data on the flow rate of the supply gas to the integration controller CX (S2).

Then, the reception part CX1 of the integration controller CX receives the data signal DS1 from the detector D1 (S3). The received data signal DS1 is input to the calculation part CX2 via the reception part CX1 of the integration controller CX.

Then, the calculation part CX2 collates the measured data included in the received data signal DS1 with the plan data corresponding to the data signal DS1 stored in the integration controller CX (S4).

This collation enables the value of the measured data to be determined to be larger than the request criteria range of the value of the plan data (S4 Yes), and the calculation part CX2 generates the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7).

The controller C1 of the recovery unit U1 adjusts, in accordance with the control signal CS1, the operation condition of the recovery unit U1 so as to increase the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to increase the amount of electric power to be supplied to the conversion unit U3 as compared with that at the measurement step (S1).

The controller C4 of the raw material supply unit U4 adjusts, in accordance with the control signal CS4, the operation condition of the raw material supply unit U4 so as to increase the flow rate of hydrogen to be supplied to the synthesis unit U5 via the flow path P4 as compared with that at the measurement step (S1).

The controller C5 of the synthesis unit U5 controls, in accordance with the control signal CS5, the operation condition of the synthesis unit U5 so as to increase the reaction temperature when synthesizing the carbon compound as compared with that at the measurement step (S1).

Thereafter, each detector measures the parameter of the object similarly to the measurement step (S1) (S8). Thus, the operation status after the adjustment is verified.

In the seventh control example, even in the case where the amount of the supply gas increases, the carbon compound to be synthesized by the synthesis unit U5 can be controlled within a fixed range. This can suppress the fluctuation in synthetic amount of the carbon compound due to the deviation in substance amount among the units without using a buffer tank.

In the seventh control example, the controller C0, the controller C2, the detector D2, the detector D3, the detector D4, the detector D5, the detector D6, the detector D7, the detector D8, and the detector D9 do not always have to be operated. In the case of operating those components, the controller C0, the controller C2, and the detectors D2, D3, D4, D5, D6, D7, D8, D9 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

Eighth Control Example

Another control example when the amount of the supply gas supplied from the emission unit U0 to the recovery unit U1 decreases to be smaller than a desired value in the system illustrated in FIG. 1 will be explained.

First, the detector D1 measures the flow rate of the supply gas supplied to the recovery unit U1 and generates the data signal DS1 (S1).

Next, the detector D1 transmits the data signal DS1 including the measured data on the flow rate of the supply gas to the integration controller CX (S2).

Then, the reception part CX1 of the integration controller CX receives the data signal DS1 from the detector D1 (S3). The received data signal DS1 is input to the calculation part CX2 via the reception part CX1 of the integration controller CX.

Then, the calculation part CX2 collates the measured data included in the received data signal DS1 with the plan data corresponding to the data signal DS1 stored in the integration controller CX (S4).

This collation enables the value of the measured data to be determined to be smaller than the request criteria range of the value of the plan data (S4 Yes), and the calculation part CX2 generates the control signal CS1, the control signal CS3, the control signal CS4, and the control signal CS5 by the above calculation processing (S5). The generated control signals are transmitted from the transmission part CX3 to the controllers of the corresponding units (S6).

The corresponding units receive the control signals and execute operations on the operation conditions in accordance with the received control signals (S7).

The controller C1 of the recovery unit U1 adjusts, in accordance with the control signal CS1, the operation condition of the recovery unit U1 so as to decrease the amount of carbon dioxide to be recovered by the recovery unit U1 as compared with that at the measurement step (S1).

The controller C3 of the conversion unit U3 adjusts, in accordance with the control signal CS3, the operation condition of the conversion unit U3 so as to decrease the amount of electric power to be supplied to the conversion unit U3 as compared with that at the measurement step (S1).

The controller C4 of the raw material supply unit U4 adjusts, in accordance with the control signal CS4, the operation condition of the raw material supply unit U4 so as to decrease the flow rate of hydrogen to be supplied to the synthesis unit U5 via the flow path P4 as compared with that at the measurement step (S1).

The controller C5 of the synthesis unit U5 controls, in accordance with the control signal CS5, the operation condition of the synthesis unit U5 so as to decrease the reaction temperature as compared with that at the measurement step (S1).

Thereafter, each detector measures the parameter of the object similarly to the measurement step (S1) (S8). Thus, the operation status after the adjustment is verified.

In the eighth control example, even in the case where the amount of the supply gas decreases, the carbon compound to be synthesized by the synthesis unit U5 can be controlled within a fixed range. This can suppress the fluctuation in synthetic amount of the carbon compound due to the deviation in substance amount among the units without using a buffer tank.

In the eighth control example, the controller C0, the controller C2, the detector D2, the detector D3, the detector D4, the detector D5, the detector D6, the detector D7, the detector D8 and the detector D9 do not always have to be operated. In the case of operating those components, the controller C0, the controller C2, and the detectors D2, D3, D4, D5, D6, D7, D8, D9 each measure the parameter of the object at each part, so that when the measured data is determined to be abnormal in the integration controller CX, each part may be controlled so as to be brought into a normal state. For example, in the case of operating the controller C2, when it is determined that abnormality such as flooding has occurred in the conversion unit U3, the controller C2 adjusts the supply amount of the first raw material to be supplied from the raw material supply unit U2 to the conversion unit U3 and thereby can adjust the conversion unit U3 into a normal state.

That the configuration of the above-explained embodiments are applicable in combination. Further, parts thereof are replaceable. While certain embodiments of the present invention have been described above, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of controlling a carbon compound manufacturing system,
the system comprising:
a recovery unit configured to separate carbon dioxide from a supply gas containing the carbon dioxide;
a conversion unit configured to convert the carbon dioxide supplied from the recovery unit into an intermediate compound;
a synthesis unit configured to synthesize a carbon compound using the intermediate compound supplied from the conversion unit;
an emission unit configured to discharge the supply gas;
a first flow path for supplying the supply gas to the recovery unit, the first flow path connecting the recovery unit and the emission unit;
a second flow path connecting the recovery unit and the conversion unit;
a third flow path connecting the conversion unit and the synthesis unit;
a first detector configured to measure a flow rate of the supply gas flowing from the emission unit to the recovery unit through the first flow path to generate a first data signal;
a second detector configured to measure a flow rate of the carbon dioxide flowing through the second flow path to generate a second data signal;
a third detector configured to measure a value of voltage or current supplied to the conversion unit to generate a third data signal; and
an integration controller, the method comprising:

generating the first to third data signals and transmitting the first to third data signals to the integration controller; and collating measured data in the first to third data signals with a plan data corresponding to the measured data by the integration controller to generate a first control signal for adjusting an operation condition of the recovery unit, a second control signal for adjusting an operation condition of the conversion unit, and a third control signal for adjusting an operation condition of the synthesis unit by calculation processing when a value of the measured data is outside a request criteria range of a value of the plan data.

2. The method according to claim 1, wherein:

the system further comprises at least one raw material supply unit selected from the group consisting of a first raw material supply unit configured to supply to the conversion unit a first raw material for converting the carbon dioxide into the intermediate compound, and a second raw material supply unit configured to supply to the second flow path a second raw material for synthesizing the carbon compound; and the integration controller generates the first control signal, the second control signal, the third control signal, a fourth control signal for adjusting an operation condition of the first raw material supply unit, and a fifth control signal for adjusting an operation condition of the second raw material supply unit, according to a collation result.

3. The method according to claim 2, wherein when the value of the measured data in the third data signal is larger than the request criteria range of the value of the plan data, the operation condition of the recovery unit is adjusted to increase an amount of carbon dioxide to be recovered by the recovery unit according to the first control signal, the operation condition of the conversion unit is adjusted to increase a conversion amount of carbon dioxide to be converted by the conversion unit according to the second control signal, and the operation condition of the second raw material supply unit is adjusted to decrease a flow rate of the second raw material to be supplied to the second flow path according to the fifth control signal.

4. The method according to claim 2, wherein when the value of the measured data in the third data signal is smaller than the request criteria range of the value of the plan data, the operation condition of the recovery unit is adjusted to decrease an amount of carbon dioxide to be recovered by the recovery unit according to the first control signal, the operation condition of the conversion unit is adjusted to decrease a conversion amount of carbon dioxide to be converted by the conversion unit according to the second control signal, and the operation condition of the second raw material supply unit is adjusted to increase a flow rate of the second raw material to be supplied to the second flow path according to the fifth control signal.

5. The method according to claim 2, wherein when the value of the measured data in the first data signal is larger than the request criteria range of the value of the plan data, the operation condition of the recovery unit is adjusted to increase an amount of carbon dioxide to be recovered by the recovery unit according to the first control signal, the operation condition of the conversion unit is adjusted to increase a value of volume or current to be supplied to the conversion unit according to the second control signal, and the operation condition of the second raw material supply unit is adjusted to decrease a flow rate of the second raw material to be supplied to the second flow path according to the fifth control signal.

6. The method according to claim 2, wherein when the value of the measured data in the first data signal is smaller than the request criteria range of the value of the plan data, the operation condition of the recovery unit is adjusted to decrease an amount of carbon dioxide to be recovered by the recovery unit according to the first control signal, the operation condition of the conversion unit is adjusted to decrease a value of voltage and current to be supplied to the conversion unit according to the second control signal, and the operation condition of the second raw material supply unit is adjusted to increase a flow rate of the second raw material to be supplied to the second flow path according to the fifth control signal.

7. The method according to claim 2, wherein when the value of the measured data in the first data signal is larger than the request criteria range of the value of the plan data, the operation condition of the recovery unit is adjusted to increase an amount of carbon dioxide to be recovered by the recovery unit according to the first control signal, the operation condition of the conversion unit is adjusted to increase a value of volume or current to be supplied to the conversion unit according to the second control signal, the operation condition of the second raw material supply unit is adjusted to increase a flow rate of the second raw material to be supplied to the second flow path according to the fifth control signal, and the operation condition of the synthesis unit is adjusted to increase a reaction temperature when synthesizing the carbon compound according to the third control signal.

8. The method according to claim 2, wherein when the value of the measured data in the first data signal is smaller than the request criteria range of the value of the plan data, the operation condition of the recovery unit is adjusted to decrease an amount of carbon dioxide to be recovered by the recovery unit according to the first control signal, the operation condition of the conversion unit is adjusted to decrease a value of voltage and current to be supplied to the conversion unit according to the second control signal, the operation condition of the second raw material supply unit is adjusted to increase a flow rate of the second raw material to be supplied to the second flow path according to the fifth control signal, and the operation condition of the synthesis unit is adjusted to decrease a reaction temperature when synthesizing the carbon compound according to the third control signal.

* * * * *